United States Patent
Elliott et al.

(10) Patent No.: US 10,967,205 B2
(45) Date of Patent: Apr. 6, 2021

(54) OXYGEN FLOW INDICATOR USING FLOW-POWERED ILLUMINATION

(71) Applicant: B/E AEROSPACE, INC., Wellington, FL (US)

(72) Inventors: Andrew Elliott, Shawnee, KS (US); Mrinal Nagrecha, Wichita, KS (US)

(73) Assignee: B/E Aerospace, Inc., Winston Salem, NC (US)

( * ) Notice: Subject to any disclaimer, the term of this patent is extended or adjusted under 35 U.S.C. 154(b) by 1266 days.

(21) Appl. No.: 15/212,220

(22) Filed: Jul. 16, 2016

(65) Prior Publication Data
US 2016/0325123 A1   Nov. 10, 2016

Related U.S. Application Data

(63) Continuation-in-part of application No. 14/573,966, filed on Dec. 17, 2014, now Pat. No. 10,016,632.
(Continued)

(51) Int. Cl.
*A62B 9/00* (2006.01)
*A62B 7/14* (2006.01)
(Continued)

(52) U.S. Cl.
CPC ............. *A62B 9/006* (2013.01); *A62B 7/12* (2013.01); *A62B 7/14* (2013.01); *A62B 18/02* (2013.01);
(Continued)

(58) Field of Classification Search
CPC .. A62B 7/12; A62B 7/14; A62B 9/006; A62B 18/02; A62B 18/025; B64D 2013/0681; B64D 2013/0655
See application file for complete search history.

(56) References Cited

U.S. PATENT DOCUMENTS 4,109,509 A * 8/1978 Cramer ............... A62B 7/14
                                                        128/204.22
5,005,572 A    4/1991 Raemer et al.
(Continued)

FOREIGN PATENT DOCUMENTS

CA       2789336       6/2010
CN    100573058 C    12/2009
(Continued)

OTHER PUBLICATIONS

Final Office Action on U.S. Appl. No. 14/573,966 dated Dec. 12, 2017. 7 pages.
(Continued)

*Primary Examiner* — Valerie L Woodward
(74) *Attorney, Agent, or Firm* — Locke Lord LLP; Scott D. Wofsy; Joshua L. Jones

(57) ABSTRACT

In one embodiment of an aircraft emergency oxygen delivery system, power can be generated by the flow of gas over a transducer disposed inside an oxygen delivery tube. A pressure differential gives rise to a temperature difference across the transducer, and the temperature difference can be converted to a voltage. The voltage can be quadratically dependent upon the Mach number M (e.g. flow velocities from 1 to 140 m/s) and proportional to a Seebeck coefficient of the transducer. The power thus generated may be used to operate LED indicators visible from the exterior of the tube, a variety of sensors, and wireless communication with a central control system. Oxygen flow to a mask may be adjusted based on ambient oxygen content and data collected from a passenger wearing the mask, including a blood oxygen saturation level, pulse or respiration rate.

11 Claims, 7 Drawing Sheets

Related U.S. Application Data

(60) Provisional application No. 61/918,974, filed on Dec. 20, 2013.

(51) Int. Cl.
| | | |
|---|---|---|
| *A62B 18/02* | (2006.01) | |
| *A62B 7/12* | (2006.01) | |
| *G01F 1/28* | (2006.01) | |
| *G01P 13/00* | (2006.01) | |
| *A61M 16/06* | (2006.01) | |

(52) U.S. Cl.
CPC .............. *A62B 18/025* (2013.01); *G01F 1/28* (2013.01); *G01P 13/0006* (2013.01); *A61M 16/06* (2013.01); *A61M 2202/0208* (2013.01)

(56) References Cited

U.S. PATENT DOCUMENTS

| | | | |
|---|---|---|---|
| 5,572,994 A | 11/1996 | Smith | |
| 5,857,460 A | 1/1999 | Popitz | |
| 6,331,438 B1 | 12/2001 | Aylott et al. | |
| 6,910,481 B2 | 6/2005 | Kimmel et al. | |
| 7,298,280 B2 | 11/2007 | Voege et al. | |
| 7,718,130 B1 | 5/2010 | Shinar et al. | |
| 7,730,847 B1 | 6/2010 | Redd et al. | |
| 7,925,143 B1 | 4/2011 | Lapwood | |
| 2001/0029340 A1* | 10/2001 | Mault ................... | A61M 16/08 600/532 |
| 2003/0101997 A1* | 6/2003 | Farin ........................ | A62B 7/14 128/205.17 |
| 2005/0115565 A1* | 6/2005 | Geary ................... | B64D 13/06 128/205.11 |
| 2005/0126570 A1* | 6/2005 | Phillips .................... | A62B 7/14 128/205.11 |
| 2006/0191353 A1* | 8/2006 | Sood ........................ | G01F 1/20 73/861.02 |
| 2007/0144597 A1* | 6/2007 | Cazenave .............. | B64D 25/00 137/899.2 |
| 2009/0260631 A1* | 10/2009 | Aubonnet ................ | A62B 9/02 128/205.25 |
| 2010/0012123 A1* | 1/2010 | Rittner ..................... | A62B 7/14 128/204.21 |
| 2011/0220116 A1* | 9/2011 | Lowenstein ........ | A61M 16/044 128/207.14 |
| 2012/0325215 A1* | 12/2012 | Levenick .............. | A61M 16/08 128/205.23 |
| 2013/0312743 A1* | 11/2013 | Kshirsagar ............ | B64D 11/00 128/202.26 |

FOREIGN PATENT DOCUMENTS

| | | |
|---|---|---|
| EP | 1 099 910 A2 | 5/2001 |
| FR | 2654057 A1 | 5/1991 |
| WO | WO-2007/096181 A1 | 8/2007 |
| WO | WO-2008/008324 A2 | 1/2008 |
| WO | WO 2008/109929 A1 | 9/2008 |

OTHER PUBLICATIONS

Office Action on Canadian Patent Application No. 2,915,813 dated Apr. 19, 2018. 3 pages.
Office Action on Canadian Patent Application No. 2,933,615 dated Apr. 19, 2018. 3 pages.
Office Action on Canadian Patent Application No. 2915813 dated Aug. 11, 2017. 3 pages.
Office Action on Chinese Patent Application No. 201480069608.8 dated May 3, 2018. 8 pages.
U.S. Notice of Allowance on U.S. Appl. No. 14/573,966 dated Mar. 1, 2018. 5 pages.
Non-Final Office Action on U.S. Appl. No. 14/573,966, dated May 5, 2017, 13 pages.
Office Action of European Patent Office Application No. 14736564.7, dated Jun. 8, 2017, 5 pages.
Second Office Action (with translation) of Chinese Patent Application No. 201480034838.0, dated Jun. 16, 2017, 5 pages.
International Search Report dated Apr. 30, 2015 in PCT/US2014/071722, published as WO 2015/095823 on Jun. 25, 2015, 5 pages.
Second Office Action on Chinese Patent Application No. 2014800696088 dated Oct. 9, 2018. 4 pages.

\* cited by examiner

OXYGEN FLOW INDICATOR USING FLOW-POWERED ILLUMINATION

CROSS-REFERENCES TO RELATED APPLICATIONS

This application is a continuation in part of U.S. application Ser. No. 14/573,966 filed Dec. 17, 2014 which claims priority from U.S. Application No. 61/918,974, filed Dec. 20, 2013, the content of which is incorporated by reference in its entirety.

BACKGROUND

The present disclosure relates generally to an oxygen delivery system for airline passengers, medical patients, emergency rescue personnel, and the like, and more particularly to an indicator tube configured to detect a flow of oxygen from an oxygen supply to an oxygen mask.

U.S. Pat. No. 7,730,847 to Redd et al., incorporated fully herein by reference, discloses a disposable breathing apparatus with a flow indicator that is located proximal to the mask for easy confirmation of the operational status of the system. Redd teaches the need for confirmation of the flow of oxygen at the mask as opposed to the source of the oxygen. U.S. Pat. No. 7,298,280 to Voege, et al., incorporated fully herein by reference, discloses a fluid flow indicator for monitoring and indicating fluid flow wherein the fluid pressure activates a pressure switch to indicate the presence of fluid movement in a tube or conduit. In a preferred embodiment, the pressure switch is observable from outside the conduit so that flow can be verified to a patient, passenger, or other fluid recipient.

SUMMARY

In one embodiment of an aircraft emergency oxygen delivery system, power can be generated by the flow of gas over a transducer disposed inside the oxygen delivery tube. A pressure differential gives rise to a temperature difference across the transducer, and the temperature difference can be converted to a voltage. The voltage can be quadratically dependent upon the Mach number M (e.g. flow velocities from 1 to 140 m/s) and proportional to a Seebeck coefficient of the transducer. The power thus generated may be used to operate LED indicators visible from the exterior of the tube, a variety of sensors, and wireless communication with a central control system. Oxygen flow to the mask may be adjusted based on ambient oxygen content and data collected from the passenger wearing the mask, including a blood oxygen saturation level, pulse or respiration rate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF ILLUSTRATIVE EMBODIMENTS

Figure 1A:
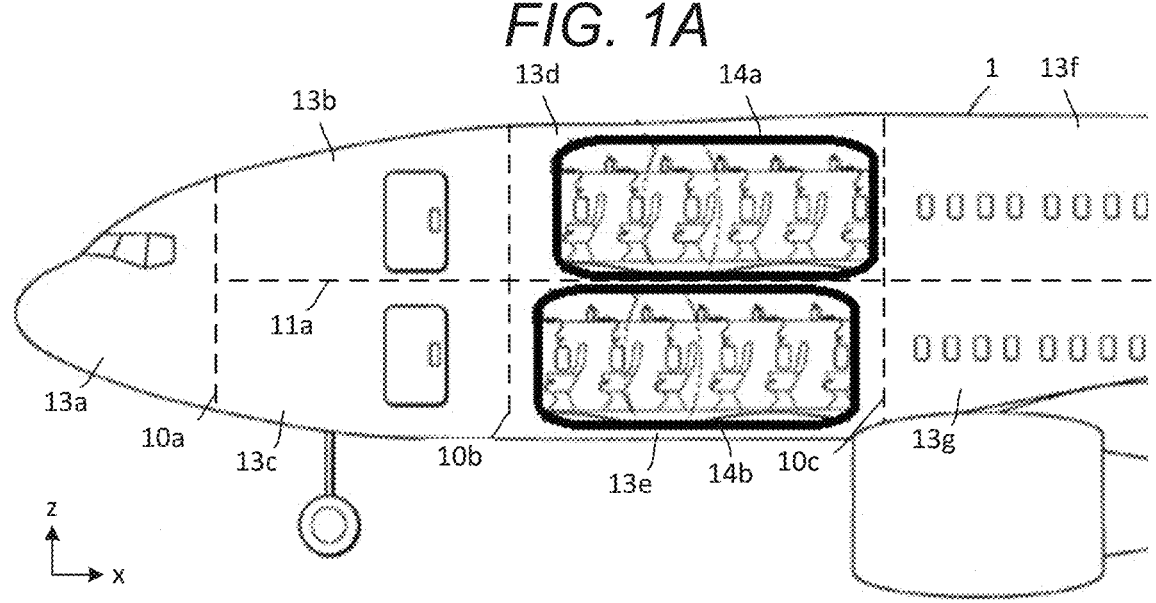
FIG. 1A illustrates an aircraft in a x-z plane, divided into different cabin sections in an x-direction and a z-direction, with a cabin section partially cut-away showing a number of passenger seats according to an example.

In selected embodiments an oxygen delivery system includes an indicator tube configured to indicate a local concentration of oxygen and a method for dispensing oxygen to a crew and set of passengers based on the local concentration of oxygen. The indicator tube can be configured to simultaneously sense and transduce a flow of oxygen, from an oxygen source to an oxygen mask, into power such that an indicator on the indicator tube is illuminated and visible to the crew and the passenger. In an embodiment, the indicator tube includes an indicator configured to provide a visual indication to a user when gas is flowing within the tube from the gas source to the passenger, and an energy harvester configured to provide energy captured from the gas flow.

The indicator tube can utilize one or a plurality of the techniques described herein to generate energy utilizing a flow present in tubing/piping that connect a manifold for dispensing breathing oxygen or air to a mask, cannula or other oral/oral-nasal device.

A first preferred method of power generation is the direct generation of a voltage and current by gas flow over carbon nanotubes and semiconductors. By employing Bernoulli's principle coupled with the Seebeck effect, a voltage and current can be generated by utilizing a gas flow over a layer of doped silicon/germanium, applied to single/multiwall carbon nanotubes. U.S. Pat. No. 7,302,845 to Sood et al, entitled "Method for measurement of gas flow velocity, method for energy conversion using gas flow over solid material, and device therefor" describes one such method an is incorporated herein by reference.

Transduced energy generated can be used to in energy conversion devices and, more importantly, gas flow sensors.

Using a clamp, multi-part system, or insert with an angle incident to a flow direction, the gas flow induces a pressure differential (and consequently temperature differential) that in turn generates a voltage/current. The voltage may be generated even by a very slow flow, and this voltage is employed in the oxygen delivery system in conjunction with an illumination device (e.g. luminescent paint, LED's, OLED's, etc.) that requires low power, to generate a visual indication when there is flow passing through this system.

Referring now to the drawings, wherein like reference numerals designate identical or corresponding parts throughout the several views.

Figure 1B:
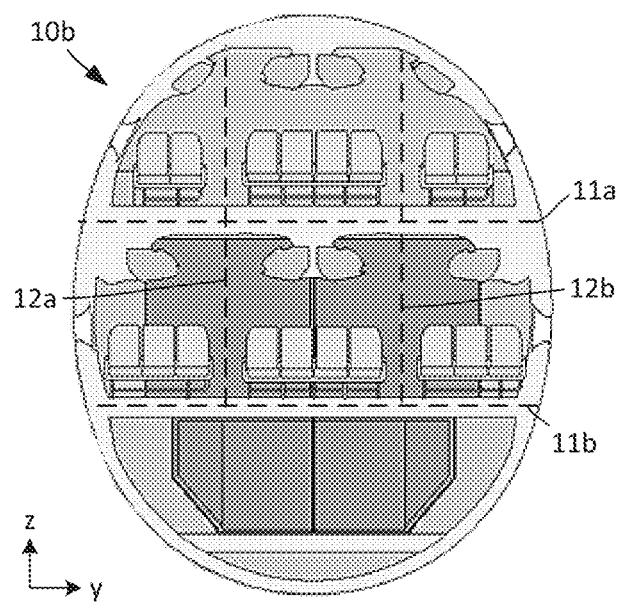
FIG. 1B illustrates a cross-section of an aircraft in a y-z plane, divided into different cabin sections in an y-direction and a z-direction according to an example.

FIGS. 1A-B illustrate an aircraft divided into different cabin sections 13a-f with two cabin sections 13d-e partially cut-away showing a number of passenger seats 2 in each cabin section according to an example. In an example, the cabin sections 13a-f can be defined and divided in a longitudinal direction 10a-c along a length of the airplane, in a horizontal direction 12a-b along a width of the airplane, and in a vertical direction 11a-b along a height of the airplane.

The airplane can have a centralized oxygen delivery system or a set of distributed oxygen delivery systems. In an example, the centralized oxygen delivery system can be configured to serve all cabin sections, whereas the set of distributed oxygen delivery systems can be configured to serve one or more cabin sections. In further example, each distributed oxygen delivery system can be configured to serve a partial cabin section such as a row of seats 2a-c (See FIG. 1C).

Each cabin section and partial cabin section can have a local oxygen concentration level (%), which may be different. For example, a cabin section below the horizontal line 11b where luggage is stored may not require a same oxygen concentration level as a cabin section holding passengers. In an example, the local oxygen concentration level can be based on a design of the oxygen delivery system. In an example, the local oxygen concentration level can be based on a function status of the oxygen delivery system. For example, in the case of a failure of the distributed oxygen delivery system for a cabin section or partial cabin section, the local oxygen concentration level may vary as compared to a different cabin section or partial cabin section.

The local oxygen concentration level may be affected in several ways including a dynamic control of delivery based on occupancy of the cabin section and a failure event of a part of the oxygen delivery system.

In an aspect, the oxygen delivery system can be configured to compare one or more readings from one or more indicator tube 30 in order to determine a functional status of the oxygen delivery system.

Figure 2A:
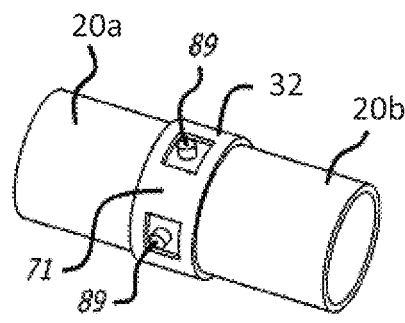
FIGS. 2A and 2B are an perspective view and cross-sectional views of an energy harvester according to an example.
Figure 2B:
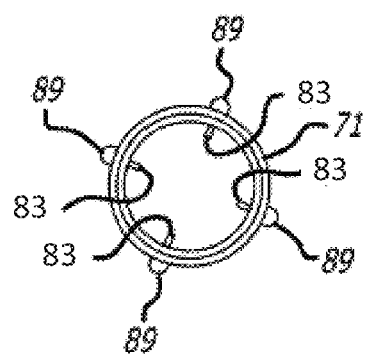

Each indicator tube 30 includes one or more indicators 89 (See FIGS. 2A-2B). The indicator 89 may be selected from the group including an LED, an LED bar graph, an LCD display, luminescent organic material, light emitting polymers, plastic scintillators, light-emitting MEMS, phosphorescent organic light emitting device (OLED), incandescent bulbs, and lasers. In an aspect, the oxygen delivery system can be configured to compare one or more measurements from one or more indicator tubes 30 in order to determine a functional status of an individual indicator tube 30, such as if there is an occlusion present. Each indicator 89 can be configured to be visible to a wearer of the mask. In an example, the indicator 89 can be configured to pulse at a rate such as to help the wearer regulate their breathing. In an example, the indicator 89 can be configured to ramp its intensity such as to glow at a rate to induce a change in the wearer's breathing (i.e. induce a calming effect).

Figure 1C:
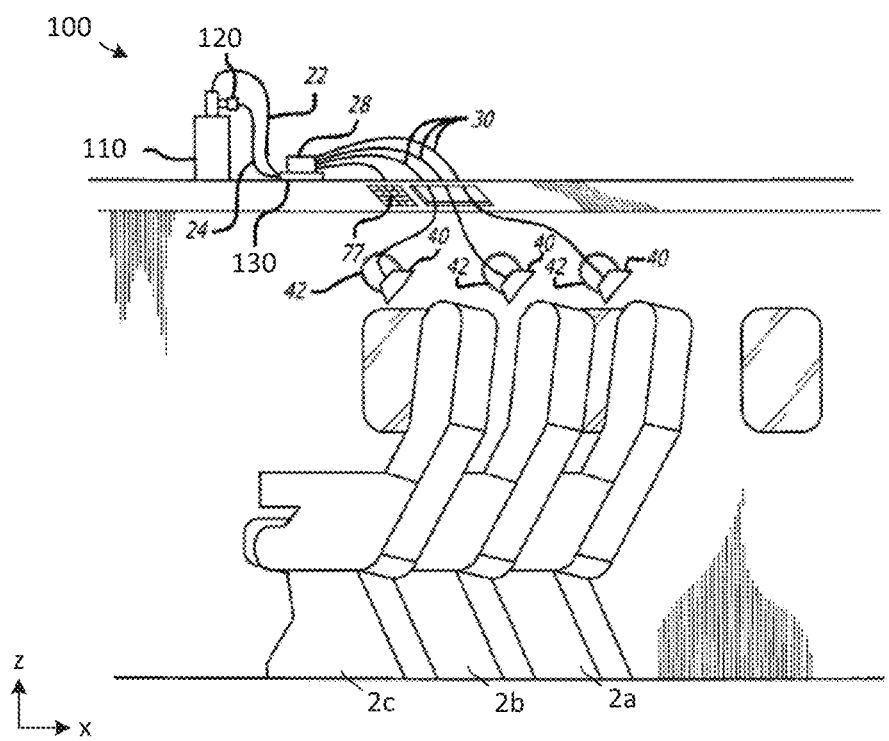
FIG. 1C illustrates a partial cabin section including a number of passenger seats and an oxygen delivery system having an oxygen source, a regulator, a controller, an indicator tube, and a mask according to an example.

FIG. 1C illustrates an oxygen delivery system 100 including an oxygen source 110 which is connected to a controller 130 electrically via cabling 22 and also with a flow tube 24 that couples to a pressure reducer/regulator 120 according to an example. Examples of pressure reducer/regulator 120 include a continuous flow regulator 322, a pulse volume regulator 324, and an integrated regulator 220 in a mask.

The indicator tube 30 can connect the mask to the oxygen delivery system, in several ways. In an example, the indicator tube 30 can be a combination of an active portion 32 and that is inserted between two pieces of passive tubing 20a-b, as shown in FIG. 2A. In an example, the active portion 32 can be an integrated piece of the tubing 20. In an example, the active portion 32 can be inserted into the passive tubing 20. The active portion 32 can be held in place by a connector, by friction, or any other method to couple the passive tubing 20.

In an example, the indicator tube 30 can be powered in several ways including directly, wirelessly, and by transducing or harvesting energy. In an example, the indicator tube 30 can transduce power from the flow of air. In an example, the indicator tube 30 can transduce power from the flow of oxygen such that the indicator 89 is only powered when oxygen is flowing.

Figure 1D:
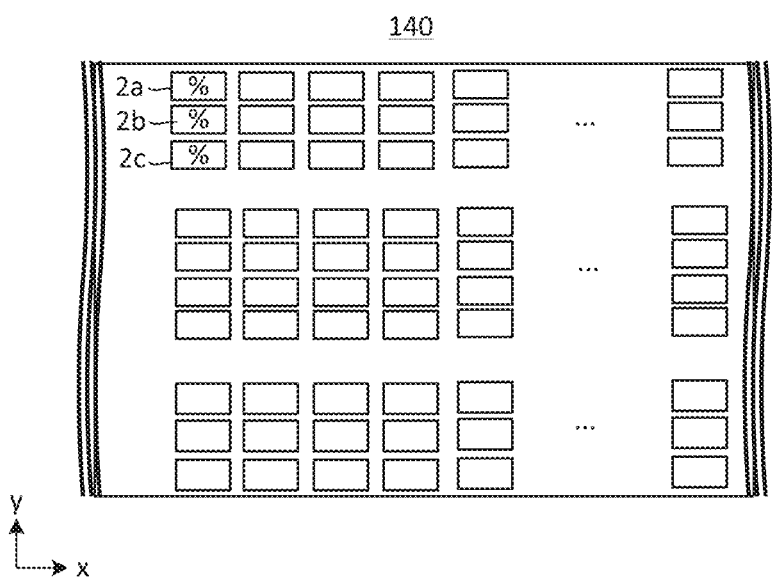
FIG. 1D shows an indicator panel including a local oxygen concentration level indicator at each passenger seat according to an example.

In an example, the indicator tube 30 can include an RFID (not shown) which can be configured to communicate the measurement from a sensor or a status of an indicator for each passenger which can be aggregated to an indicator panel 140 for the entire cabin (See FIG. 1D).

As shown in FIGS. 2A and 2B, the indicator tube 30 can have a housing 71 that is configured to connect to the tubing 20a-b, one or more energy harvesters 83 located within the housing 71, and one or more indicators 89 configured to be illuminated by power generated from the one or more energy harvesters 83 when breathing-gas flows past the energy harvester. In an example, a sensor can be powered by a mechanical energy harvester such as a paddlewheel, a turbine, a screw, and a set of fan blades.

Figure 2C:
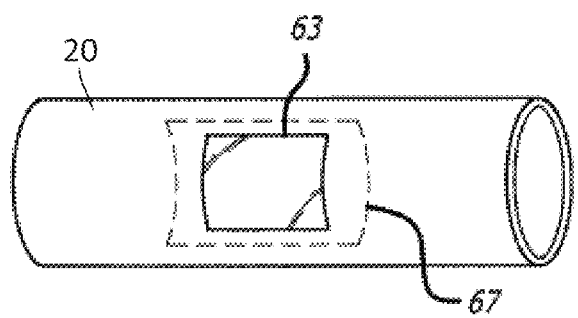
FIG. 2C is a perspective view of an indicator tube including a photo-luminescent film and a magnifier according to an example.

As shown in FIG. 2C, the indicator tube 30 may also include a sensor that is an oxygen-sensing film 67 on an inner portion interfacing with the flow of air and a magnifier 63 configured to augment visibility of a color of the oxygen-sensing film 67. The oxygen-sensing film 67 can include oxygen-sensitive materials that have a photoluminescence property such as Pt-octaethylporphyrin or Pd-octaethylporphyrin embedded in polystyrene and tris(4,7-diphenyl-1,10-phenanthroline) RuII (Ru(dpp)) embedded in a sol-gel film.

The oxygen-sensing film 67 can include a photoluminescent dye having a photoluminescence intensity I and a photoluminescence lifetime $\tau$, where its photoluminescence property is based on a dynamic quenching of the photoluminescent dye according to an example. The photoluminescent dye may also utilize a chemical that is reactive to oxygen and can be used to detect the presence and concentration of oxygen. Alternatively, the photoluminescent dye may utilize chemical compounds that are reactive to oxygen, but do not create any new compounds or reaction byproducts that are harmful to the human body when inhaled.

In an example, oxygen detection can be done by monitoring the photoluminescence intensity I, in a DC mode. In an example, oxygen detection can be done by monitoring the photoluminescence lifetime $\tau$, in a pulse mode. A response time for oxygen detection is much faster in the pulse mode (<100 ns) as compared to the dc system (0.5-1000 $\mu$s), both of which provide sufficient resolution for oxygen detection in the aforementioned applications.

Figure 4A:
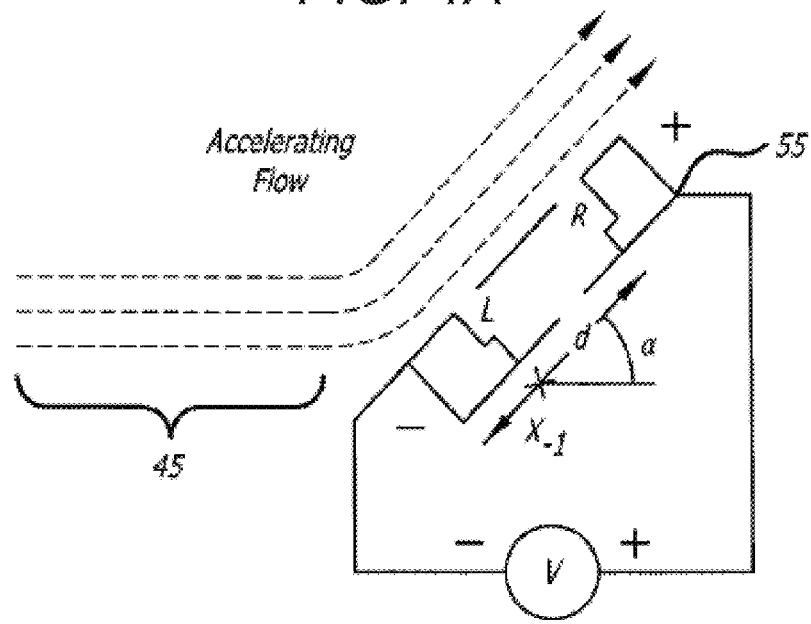
FIG. 4A is a schematic of a gas flow impinging on a transducer according to an example.
Figure 4B:
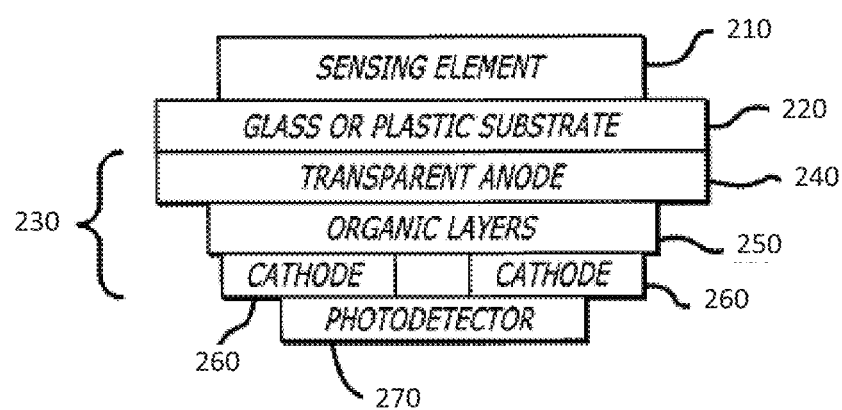
FIG. 4B is a cross-section of an oxygen sensor according to an example.

As shown in FIG. 4B, a combined sensor and indicator 56 can include a sensing element 210 embedded on a glass or plastic substrate 220, an OLED component 230 that includes an anode 240, a set of organic layers 250, and a cathode(s) 260, followed by a photodetector layer 270. A photo-luminescent sensor, when integrated with the OLED component, can currently produce functional lifetimes of over 20,000 hours for certain emitters.

In an example, the sensor can utilize a transducing material, such as single/multiwall carbon nanotubes or doped silicon/germanium, placed at an angle configured to generate a pressure differential in order to induce a temperature differential and consequently produce energy in the transducing material to then illuminate the indicator. The thermovoltaic power generation can be utilized in areas throughout an aircraft cabin including environmental control systems, air gaspers/ducts, pressurization equipment and can be configured to harvest or generate and store power for the purposes of life support systems.

As shown in FIG. 2C, the magnifier 63 is configured to augment visibility of a color of the oxygen-sensing film 67. In another example, the magnifier 63 can be used to increase a range and condition under which the indicator 89 can illuminate through. The magnifier 63 may also have portions with one or a plurality of colors such that the indicator 89 is configured to have a different color based on a location of the indicator 89 in the indicator tube 30. In an example, the magnifier can include an illuminated source (not shown) such as an LED, OLED, and a luminescent coating.

The oxygen-sensing film 67 can be inserted anywhere along the indicator tube, thereby reducing a number of connections while maintaining a level of service provided.

A direct generation of usable power can be transduced when a gas is passed over a transducer even at a modest speed of a few meters per second. The underlying mechanism involves both Bernoulli's principle and the Seebeck effect. A pressure difference along streamlines give rise to a temperature difference across the transducer, and the temperature difference can be converted to a voltage. The voltage can be quadratically dependent upon the Mach number M (e.g. flow velocities from 1 to 140 m/s), and proportional to a Seebeck coefficient of the transducer.

The transducer can be made of materials including doped Silicon (Si) and Germanium (Ge), such as n-type Ge doped with Antimony (Sb), n and p-type Silicon, as well as carbon nanotubes such as single wall and multiwall carbon nanotubes, graphite as well as doped semiconductors/metals.

FIG. 4A depicts a flow of a gas 45 impinging a transducer 55 having a left terminal L and a right terminal R. In an example, a flow impingement angle, α=45°, with respect to the horizontal axis, is shown, producing a greatest differential in pressure, and consequently in temperature, between the two terminals L, R, coated with silver emulsion to effectively yield the greatest amount of voltage V in the system. This effect is described by Bernoulli's equation as follows in Equation 1:

$$\frac{P_0}{P} = \left[1 - \frac{1}{2}(\gamma-1)M^2\right]^{\gamma/(\gamma-1)} \cong 1 - \frac{\gamma}{2}M^2 (\text{for } \gamma M^2 \ll 1)$$

where γ is the ratio of specific heat of a gas at a constant pressure to heat at a constant volume. Equation 1 is valid for an adiabatic, steady inviscid flow of a gas, and provides a pressure difference that can be converted into a temperature difference using the ideal gas law in order to estimate the energy produced by the flow. For the case shown in FIG. 4A, the temperature differential can be written as $$\frac{\Delta T}{T_0} \cong \frac{1}{2}(\gamma-1)(M_R^2 - M_L^2),$$

where the subscripts indicate the left terminal L and a right terminal R, as shown in FIG. 2A. The temperature difference causing a voltage difference is described as the Seebeck effect, and the relationship between voltage generated and the Seebeck effect is given by Equation 3:

$$V = \frac{kT_0}{2}(\gamma-1)S(M_R^2 - M_L^2) \propto \frac{kT_0}{2}(\gamma-1)SM^2$$

which describes the relationship between Mach number M and voltage V, and correspondingly provided the Seebeck coefficient for the materials.

In an example, the Stern-Volmer equation (4) can be used to measure a change in the concentration of oxygen as a current:

$$\frac{I_0}{I} = \frac{\tau_0}{\tau} = 1 + K_{SV}[O_2] \tag{4}$$

I is the photoluminescence intensity, τ is the photoluminescence lifetime, and $K_{sv}$ is the Stern-Volmer constant of the photoluminescent dye.

The photoluminescent dye can be integrated with OLEDs that are of low-weight, low-voltage, flexible, and miniaturizable. OLEDs also lend themselves well to such applications due to the ease of manufacturability onto glass and plastic substrates in sizes in the order of micrometers to millimeters. The oxygen-sensing film 67 can be fabricated in the order of millimeters where the OLED component is less than half a micrometer.

Figure 3A:
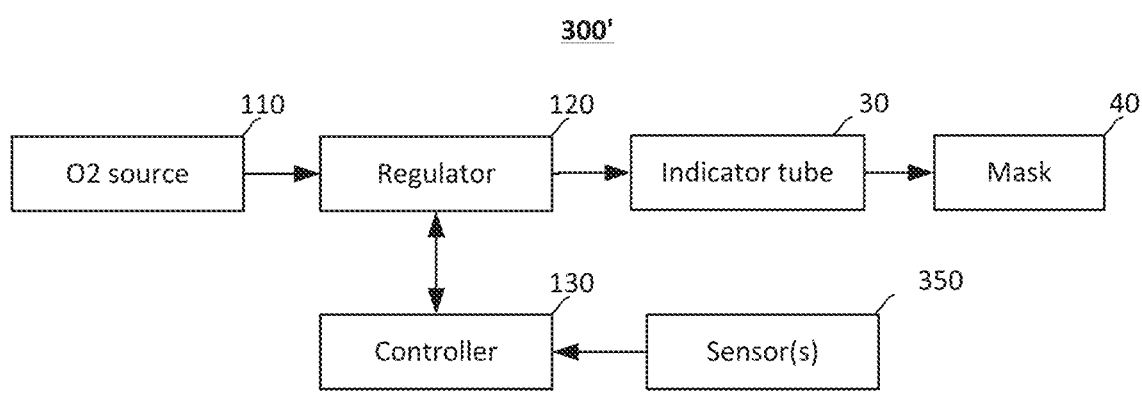
FIG. 3A is a schematic diagram of an oxygen delivery system including the oxygen source, the regulator, the controller, the mask according to an example.

FIG. 3A is a schematic diagram of an oxygen delivery system 300' including the oxygen source 110, a regulator 120, a controller 130, an indicator tube 30, a mask 40, and one or more sensors according to an example. In an aspect, the controller 130 can be configured to operate in an open loop operation until a feedback control operation is activated. The feedback control operation can be activated based on predetermined period of in-range readings according. For example, the controller can operate in an open loop fashion until the controller receives a predetermined number of readings over a predetermined period of time which are within a predetermined range which is considered indicative of actual oxygen concentration readings.

In another aspect, the controller can be configured to calculate a series of running averages based on the one or more sensors. In an example, the controller can be configured to detect and remove erroneous signals from the series of running averages. In an example, the controller can be configured to determine that the sensor data is erroneous based on sensor data from a different sensor.

The controller 130 can be a stand-alone processing device (e.g., microchip, system on a chip, processor, etc.) or be a remote element of another processing system such as a central control system. Likewise, functions of the controller 130 can be done by a single unit such as a microcontroller or by a distributed and/or hierarchical processing network.

A single controller 130 may be dedicated to a particular oxygen delivery system (e.g., unit or mask) or control a set of oxygen delivery systems (e.g., a panel of mask corresponding to a row or section of passenger seats, etc.). The controller 130 can include a processor or circuitry for generating and adjusting a running average of the oxygen concentration level, and for generating an output signal that is a function of the running average. The processor can be configured to perform checks for identifying possibly invalid output signal values and being responsive to the oxygen concentration level output signal values for evaluating a series of the oxygen concentration level output signal values and, based on the evaluation, providing a processed output signal. In the event of error detection, optionally a substitute output signal can be generated for each of the possibly invalid output signal values thereby forming a sequence of valid output signals. The processor can be configured to perform signal artifact recognition for identifying possibly invalid output signal values, and for providing a sequence of valid output signal values, exclusive of the identified possibly invalid output signal values; and means for generating a running average of the sequence of valid output signal values and for providing the running average as the processed output signal.

The controller 130 may also include or be coupled to a wireless controller (not shown), which is in turn attached to an antenna. The controller may wirelessly communicate with the central controller to send and receive data. For instance, the controller 130 may transmit data reflecting i) oxygen concentration or saturation inside the tubing, external to the tubing, or in the passenger's blood stream, ii) gas flow rate inside the tube, iii) passenger respiration rate, and iv) alerts and notifications concerning flow rates, oxygen concentration or passenger respiration rate. The controller 130 may receive from a remote central controller data reflecting i) a command to illuminate an LED in a certain manner (e.g. pulse on/off or illuminate in a certain color), ii) a command to active certain sensors (e.g., a blood saturation sensor) which were previously inactive to conserve power.

In one embodiment, data from adjacent seats is used to validate data from a given sensor or determine ambient conditions. For instance, if oxygen concentration or pressure sensors on the exterior of the tube reflect an ambient pressure or oxygen concentration that differs substantially from those reported at the adjacent seats, a central control system, may ignore the aberrant data. The data from adjacent seats in a row may be averaged to determine the ambient pressure or oxygen concentration.

Figure 3B:
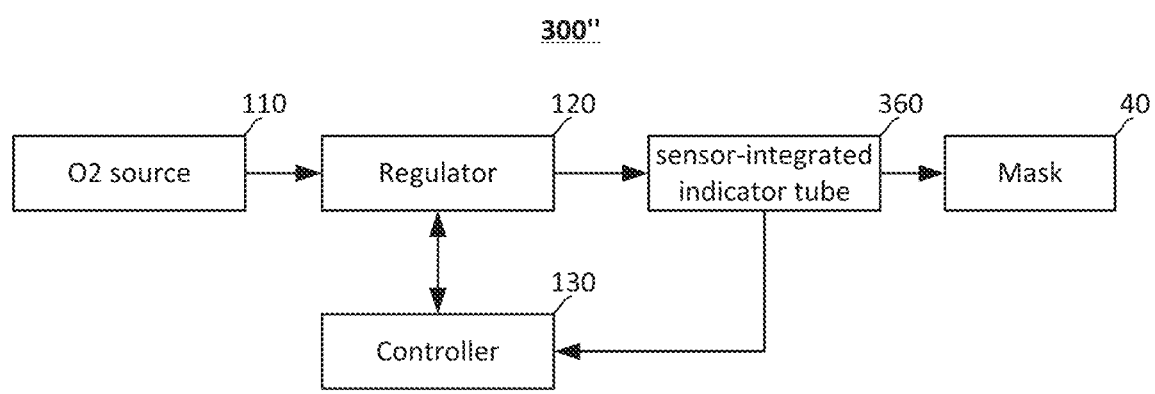
FIG. 3B is a schematic diagram of an oxygen delivery system including a sensor-integrated indicator tube according to an example.
Figure 3C:
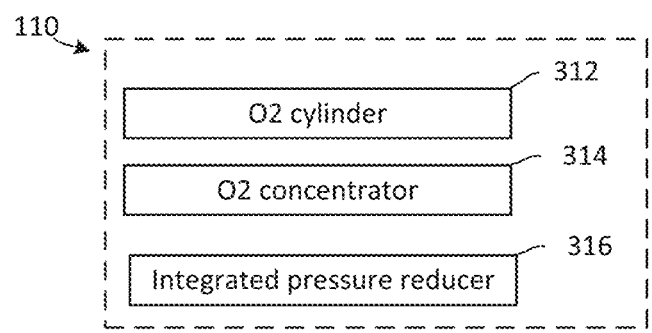
FIG. 3C shows examples of the oxygen source.
Figure 3D:
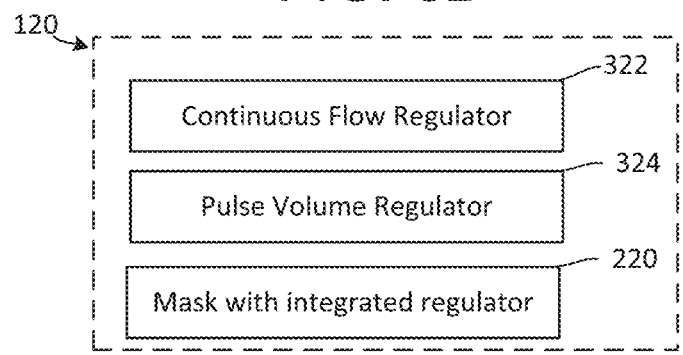
FIG. 3D shows examples of the regulator.
Figure 3E:
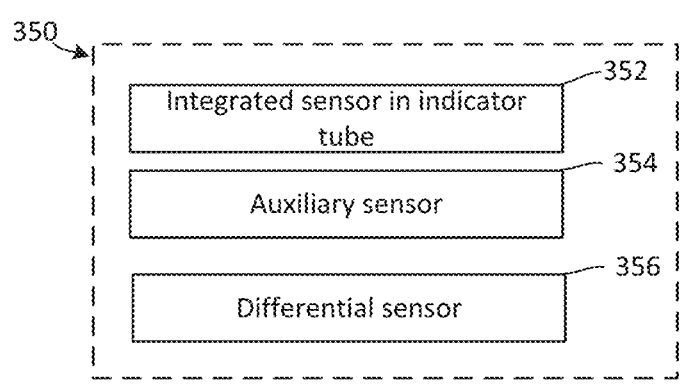
FIG. 3E shows examples of sources that can used to determine an oxygen concentration level.
Figure 5:
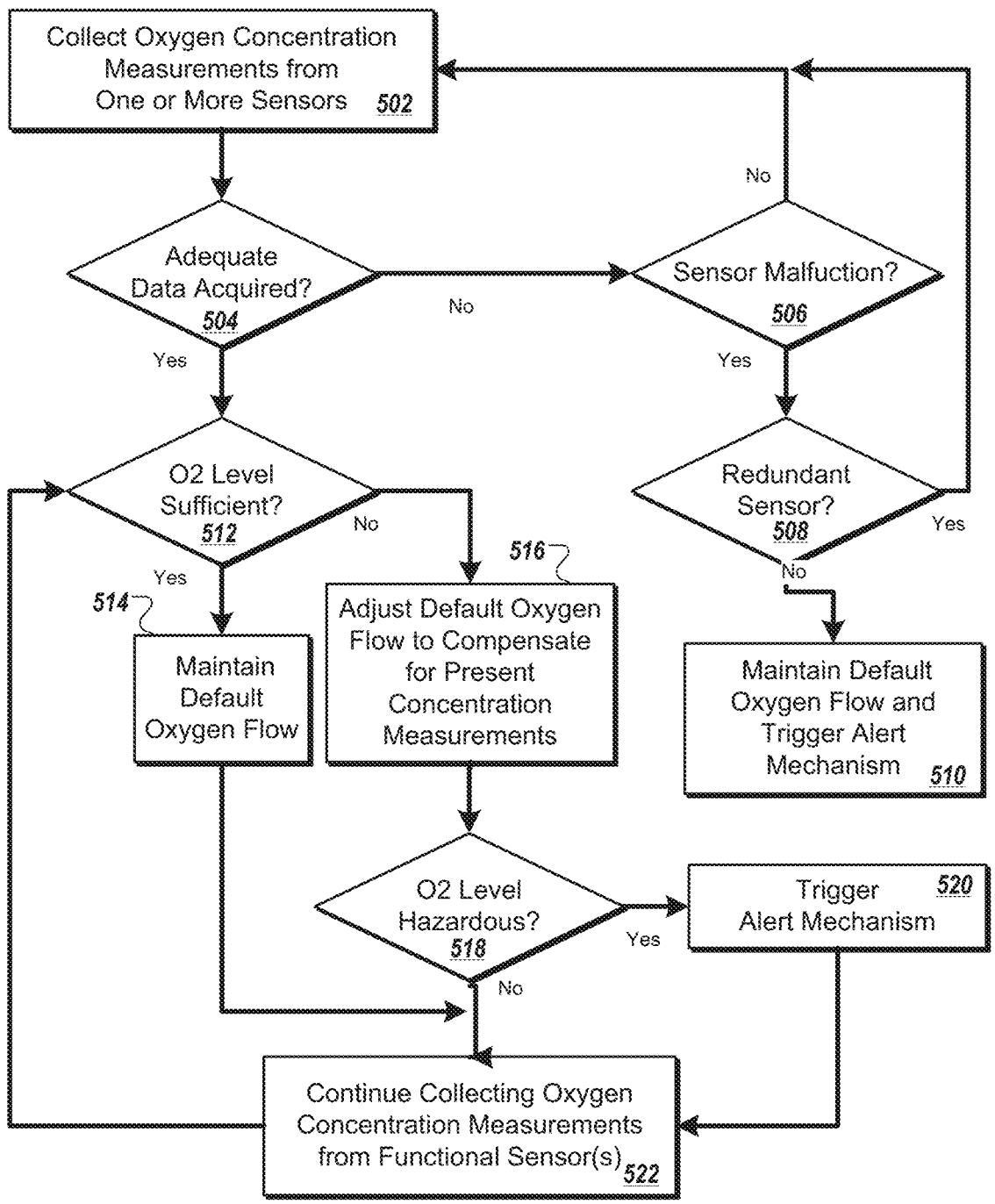
FIG. 5 is a flow chart describing a method for delivering oxygen through one or more sensor-integrated tubes on an airplane based on the local oxygen concentration level according to an example.

As illustrated in FIG. 5, a flow chart presents an example method 500 for delivering oxygen through one or more masks on an airplane based on a local oxygen concentration level. The method 500, for example, may be performed by the controller 130 illustrated in FIGS. 3A, 3B.

In some implementations, the method 500 begins with collecting local oxygen concentration level measurements from one or more sensors for an initial collection period (502). The sensors, for example, may include any type of sensor described in relation to transducer 55 of FIG. 4A, the combined sensor and indicator 56 of FIGS. 4B and 89 of FIG. 2A-2B, or sensors 350 of FIG. 3A, as well as sensors incorporated into the sensor-integrated tube 360 of FIG. 3B. In another example, a sensor can include manual input 356 via a panel 77 illustrated in FIG. 1C. The sensor data may be collected for at least a threshold period of time to establish a baseline average measurement of the local oxygen concentration level. In a particular example, the sensor data may be collected for at least one minute. In another example, the sensor data may be collected for a shortened period of time (e.g., 10, 15, or 30 seconds, etc.) to confirm that all sensors appear to be functioning. In this manner, the wearer may be alerted at an earlier stage to reposition the mask and/or sensors. In a particular example, the controller 130 (described in relation to FIGS. 3A and 3B) may evaluate sensor output signals communicated along each tubing 30 (illustrated in relation to FIG. 1C) from one or more sensors to the controller 130 and, based on the evaluation, determine a current local oxygen concentration level.

In some implementations, at the end of the initial collection period it is determined whether adequate data has been acquired (504). In one example, a first portion of the data may have been collected prior to appropriate fixation of the oxygen mask. In another example, adequacy of data may be identified by measurement of a local oxygen concentration level (external to the tubing) above or below a threshold value. In a further example, determination of inadequate data may be based upon erratic data points obtained from one or more of the sensor(s).

If it is determined that the inadequate data is not indicative of a sensor malfunction (506), in some implementations, the method 500 returns to collecting local oxygen concentration level measurements from the sensor(s) (502).

If, instead, it is determined that there is a sensor malfunction (506) providing inadequate data, in some implementations, it is determined whether there is a redundant operational sensor available (508). If there is a redundant operational sensor available (508), the method 500 may return to collecting local oxygen concentration level measurements from the redundant seasons) (502).

In some implementations, if no operational sensor is available (508), the default oxygen flow is maintained (510). For example, the oxygen flow may be based upon the altitude of the aircraft and/or a current cabin pressure. Further, in some embodiments, an alert mechanism may be triggered (510) to indicate sensor malfunction. For example, the visual indicators 89 of FIGS. 2A, 2B may be lighted, a warning sound may be issued from a speaker in communication with the controller performing the method 500, and/or a trigger mechanism may be communicated to a separate system (e.g., cockpit console) for communication of an alert to a wearer or other crew member.

Alternatively, if adequate data has been acquired (504), in some implementations, the local oxygen concentration level external to the oxygen mask and associated tubing is measured and analyzed to determine whether it is sufficient (512). This may be measured, for instance, by an oxygen saturation sensor disposed adjacent indicator 89 on the exterior of tubing 20. In normal conditions, the local oxygen concentration level in air at sea level is around 21%. In another example, maintaining a local oxygen concentration level of about or above 15% may be considered sufficient. Insufficient measurements, for example, may be anything below 15%. These percentages may be used as the aforementioned threshold values.

In some implementations, if the local oxygen concentration levels external to the tubing 20 are determined to be sufficient (512), the default oxygen flow to the oxygen mask is maintained (514). As described above, the default oxygen flow may be based upon altitude of the aircraft and/or cabin pressure.

If, instead, it is determined that the local oxygen concentration levels external to the tubing are insufficient (512), in some implementations, oxygen flow to the mask is adjusted to compensate for the present concentration measurements (516). For example, the oxygen flow rate may be calculated based upon the present local oxygen concentration level in combination with the altitude of the aircraft and/or the cabin pressure. In another example, the default oxygen flow rate (e.g., based upon the altitude of the aircraft and/or the cabin pressure) may be adjusted based upon the local oxygen concentration level. The oxygen flow rate may be determined, in some examples, using an algorithm and/or a data look-up table.

In some embodiments, additional factors may be included in determining the adjusted oxygen flow rate such as a blood oxygen saturation level of a wearer. A gas delivery system including a sensor for measuring the blood oxygen saturation level of a wearer is provided in U.S. application Ser. No. 15/192,943, filed Jun. 24, 2016, the content of which is incorporated by reference in its entirety. In some examples, the factors include i) a rate of change (e.g., decrease, increase) of blood oxygen saturation level, pulse or breathing rate over time, and/or ii) a range of blood oxygen saturation level (e.g., slightly below acceptable measurement, significantly below acceptable measurement, indicative of hazardous measurement, etc.), pulse or breathing rate. A hazardous measurement of local oxygen concentration level internal to the tubing, in one example, may be at or about 80%, while a measurement significantly below acceptable may be 81 to 85%, and a measurement slightly below acceptable may be in a range of 86 to 89%.

Regarding physiological data, in some examples, breathing rate may be obtained from inspirations of a wearer of a pulse volume regulator and/or heart rate may be obtained from the one or more sensor or from a separate heart rate sensor, depending upon particular implementation. In a particular example, if the rate of change of blood oxygen saturation level over time is considered to be moderate to rapid and/or additional physiological data is indicative of a state of unwellness, the oxygen flow rate may be increase more dramatically than otherwise. Similarly, if the local oxygen concentration level is increasing rapidly and moving close to an acceptable level, the oxygen flow rate may be decreased more dramatically (e.g., closer to the default rate). Upon determination of the adjusted rate, in a particular example, the controller 130 may issue a control signal to the oxygen flow control device 28 to deliver an additional dosage of oxygen to the wearer.

In some implementations, if local oxygen concentration levels are considered to be hazardous (518), an alert mechanism, is triggered (520), As described in relation to step 510, visual indicators may be lighted, a warning sound may be issued from a speaker in communication with the controller performing the method 500, and/or a trigger mechanism may be communicated to a separate system (e.g., cockpit console) for communication of an alert to a wearer or other crew member. In a particular example, sensor malfunction may be relayed with a visual indication. The visual indication may flash, in some embodiments, to ensure immediate attention of nearby passengers and/or crew members.

In one implementation, the controller is coupled to the indicator panel 140 such that alerts concerning a local oxygen concentration level throughout the airplane are presented on the indicator panel 140 to a pilot and/or crew. In this manner the pilot and/or crew may be alerted to a compromised local oxygen concentration level without having seen the indicators on the indicator tube.

In some implementations, whether or not the oxygen level was determined to be hazardous (518), the method 500 may continue collecting local oxygen concentration level measurements from any functional sensor(s) (522).

Although described in a particular order, on some implementations steps of the method 500 may be performed in a different order. For example, although continuing collection of local oxygen concentration level measurements (522) is illustrated as a discrete step, it should be understood that, in many embodiments, the data would be continuously collected and analyzed. Further, in some implementations, more or fewer steps may be included in the method 500. For example, in some embodiments, if additional physiological data measurements are available (e.g., breathing rate obtained from inspirations of a wearer of a pulse volume regulator, heart rate from a heart rate sensor, etc.), even if the one or more sensors are inoperable for providing consistent local oxygen concentration level measurements, the method 500 may monitor and adjust based solely on that physiological data. For example, the oxygen flow may be adjusted in an effort to improve the condition of the wearer that is causing expression of the physiological symptom(s).

It will become apparent from the foregoing that while particular forms of the invention have been illustrated and described, various modifications can be made without departing from the spirit and scope of the invention. Accordingly, it is not intended that the invention be limited by the foregoing descriptions and illustrations.

Obviously, numerous modifications and variations of the present invention are possible in light of the above teachings. It is therefore to be understood that within the scope of the appended claims, the invention may be practiced otherwise than as specifically described herein.

The invention claimed is:

1. An oxygen delivery system for delivering breathable oxygen to a plurality of masks mounted above a row of passenger seats on an airplane, the system being mounted proximate the masks and above the row of passenger seats, the system comprising:
  a regulator configured to regulate a flow of oxygen from an oxygen source;
  at least one indicator tube having:
    a proximal end connected to the regulator,
    a distal end connected to at least one mask of a plurality of masks,
    a thermo-voltaic transducer configured to transduce the flow of oxygen into power,
    a flow sensor configured to sense the flow of oxygen within at least one of a lumen of the at least one indicator tube and the at least one mask of the plurality of masks, and
    an indicator configured to illuminate based on the power transduced by the thermo-voltaic transducer, the indicator being positioned to be seen by a wearer of a respective mask of the plurality of masks;
  an ambient sensor configured to sense an ambient concentration of oxygen in the area of the passenger seats;
  a controller in communication with the regulator, the flow sensor, and the ambient sensor, the controller having processing circuitry configured to control the regulator to regulate the flow of oxygen from the oxygen source based on readings from at least one of the flow sensor and the ambient sensor, and
  an indicator panel in communication with the controller, wherein each indicator tube further comprises an RFID in communication with the controller and configured to communicate a status of at least one of the indicator and the flow sensor to the indicator panel.

2. The system of claim 1, wherein the processing circuitry is further configured to determine a functional status of the regulator based on the readings from at least one of the flow sensor and the ambient sensor.

3. The system of claim 1, wherein the processing circuitry is further configured to adjust the flow of oxygen from the oxygen supply to a respective mask based on readings from at least one of the flow sensor and the ambient sensor.

4. The system of claim 3, wherein the system comprises multiple regulators for delivering oxygen to masks above a plurality of rows of passenger seats.

5. The system of claim 1, wherein the illumination of the indicator is configured to pulse at a rate to regulate breathing of the wearer.

6. The system of claim 1, wherein each indicator tube further comprises a magnifier configured to augment visibility of the illumination of the indicator.

7. The system of claim 1, wherein the at least one indicator tube further comprises an oxygen sensing film configured to sense the flow of oxygen within at least one of a lumen of the at least one indicator tube and the at least one mask of the plurality of masks.

8. An oxygen delivery system for delivering breathable oxygen to a plurality of masks mounted above a row of passenger seats on an airplane, the system being mounted proximate the masks and above the row of passenger seats, the system comprising:
- a regulator configured to regulate a flow of oxygen from an oxygen source;
- at least one indicator tube having:
  - a proximal end connected to the regulator,
  - a distal end connected to at least one mask of a plurality of masks,
  - a thermo-voltaic transducer configured to transduce the flow of oxygen into power, and
  - a flow sensor configured to sense the flow of oxygen within at least one of a lumen of the at least one indicator tube and the at least one mask of the plurality of masks;
- an ambient sensor configured to sense an ambient concentration of oxygen in the area of the passenger seats; and
- a controller in communication with the regulator, the flow sensor, and the ambient sensor, the controller having processing circuitry configured to control the regulator to regulate the flow of oxygen from the oxygen source based on readings from at least one of the flow sensor and the ambient sensor,
  - wherein the regulator is a pulse volume regulator configured to pulse the flow of oxygen based on a reading from the ambient sensor.

9. A oxygen delivery system for distributing oxygen to a plurality of cabin sections on an airplane, the system comprising:
- an oxygen source;
- a plurality of regulators, each regulator located in a respective cabin section and having an input in communication with the oxygen source and configured to regulate a flow of oxygen from the oxygen source to a plurality of outputs;
- a plurality of indicator tubes, each indicator tube having a proximal end connected to at least one output of a plurality of outputs of a respective regulator, a distal end connected to at least one mask of a plurality of masks in the respective cabin section, and a flow sensor configured to sense the flow of oxygen within at least one of a lumen of the respective indicator tube and the at least one mask;
- a plurality of ambient sensors, each ambient sensor configured to sense an ambient concentration of oxygen in the respective cabin section, wherein each regulator is a pulse volume regulator configured to pulse the flow of oxygen based on a reading from a respective ambient sensor of the plurality of ambient sensors; and
- a controller in communication with the plurality of regulators, the plurality of indicator tubes, and the plurality of ambient sensors, the controller having processing circuitry configured to control each regulator to adjust the flow of oxygen from the oxygen supply based on readings from at least one of the plurality of indicator tubes and the plurality of ambient sensors associated with the respective regulator.

10. The system of claim 9, wherein the processing circuitry is further configured to determine a functional status of a portion of the oxygen delivery system based on the readings from at least one of the at least one indicator tube of the plurality of indicator tubes and at least one ambient sensor of the plurality of ambient sensors.

11. The system of claim 9, wherein at least one mask of the plurality of masks is in a first cabin section having a first local oxygen concentration level, and at least one other mask of the plurality of masks is in a second cabin section having a second local oxygen concentration level.

* * * * *